(12) United States Patent
Danielsson

(10) Patent No.: US 6,275,561 B1
(45) Date of Patent: Aug. 14, 2001

(54) COMPUTER TOMAGRAPHY METHOD WITH HELICOIDAL SCANNING OF AN EXAMINATION AREA

(75) Inventor: Per-Erik Danielsson, Linköping (SE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/380,972
(22) PCT Filed: Jan. 12, 1999
(86) PCT No.: PCT/IB99/00027
§ 371 Date: Sep. 10, 1999
§ 102(e) Date: Sep. 10, 1999
(87) PCT Pub. No.: WO99/36885
PCT Pub. Date: Jul. 22, 1999

Related U.S. Application Data

(63) Continuation-in-part of application No. 09/228,219, filed on Jan. 11, 1999.

(30) Foreign Application Priority Data

Jan. 13, 1998 (SE) .................................................. 9800029

(51) Int. Cl.⁷ ..................................................... G01N 23/00
(52) U.S. Cl. ............................. 378/15; 378/4; 250/363.03
(58) Field of Search ................................. 378/15, 4, 65, 378/210; 250/363.03

(56) References Cited

U.S. PATENT DOCUMENTS

| | | | |
|---|---|---|---|
| 5,323,007 | * | 6/1994 | Wernick et al. ................ 250/363.03 |
| 5,744,802 | * | 4/1998 | Muehllehner et al. ......... 250/363.03 |
| 5,828,718 | * | 10/1998 | Ruth et al. ............................ 378/19 |
| 5,848,117 | * | 12/1998 | Urchuk et al. ........................ 378/19 |

* cited by examiner

Primary Examiner—Robert H. Kim
Assistant Examiner—Pamela R. Hobden
(74) Attorney, Agent, or Firm—John F. Vodopia

(57) ABSTRACT

The invention relates to a CT method which involves helical scanning of an examination zone by means of a cone beam. Measuring data for the three-dimensional tomographic imaging of objects of arbitrary length are now acquired completely and without redundancy. The reconstruction requires only a one-dimensional filtering operation. Particularly simple processing steps are enabled by a rebinning operation during which fan beams which are situated in planes extending parallel to one another and to the axis of rotation are combined.

7 Claims, 9 Drawing Sheets

COMPUTER TOMAGRAPHY METHOD WITH HELICOIDAL SCANNING OF AN EXAMINATION AREA

This application is a continuation-in-part of application Ser. No. 09/228,219, filed Jan. 11, 1999.

BACKGROUND OF THE INVENTION

1. Field of the Invention

The invention relates to a computer tomography method which involves helical scanning of an examination zone by means of a scanning unit which includes a radiation source and a detector unit, an object present in the examination zone and the scanning unit simultaneously rotating about an axis of rotation relative to one another and performing a motion parallel to the direction of the axis of rotation, resulting in a relative motion in the form of a helix, and also involves a reconstruction of the spatial distribution of the absorption within the examination zone from the measuring data acquired by the detector unit. The invention also relates to a computer tomography apparatus for performing a method of this kind.

2. Description of the Related Art

A method and a computer tomography apparatus of the kind set forth are known from DE-OS 195 45 778 (Tam). This known method enables the scanning of an extended examination zone in the direction of the axis of rotation by means of a cone beam and the reconstruction of the absorption distribution in the examination zone also in case the object present therein, for example a patient, is longer than the part of the examination zone for which data has been acquired.

However, for this method it is necessary to define in advance the so-called region of interest (ROI) and at the beginning and at the end of the ROI (in relation to the direction of rotation) an additional scan of the examination zone must be performed along a circular path which extends perpendicularly to the axis of rotation. The reconstruction of the absorption distribution may commence only after the scanning of the examination zone has been completed. The change over from a circular scan to a helical scan and back to a circular scan of the examination zone necessitates an abrupt acceleration or deceleration of either the scanning unit or the object in the examination zone; this could cause unsharpness. It is a further drawback that the scanning region must be defined in advance.

SUMMARY OF THE INVENTION

Therefore, it is an object of the present invention to provide a method of the kind set forth which does not require additional circular scanning motions and enables the reconstruction already during the acquisition of the measuring data. This object is achieved by a method of the kind set forth in that it includes the following steps:

a) using exclusively the measuring data for the reconstruction which are obtained from rays which pass exactly through the area between two adjacent turns of the helix, the points within the examination zone thereby being irradiated over an angular range of exactly 180 degrees—as seen from the point itself, b) rebinning the measuring data and the associated rays so as to form a number of groups, each group comprising a plurality of planes which extend parallel to the axis of rotation and each of which contains a respective fan beam, c) filtering the data of each group formed by the rebinning d) reconstructing of the spatial distribution of the absorption from the filtered data of different groups.

The invention utilizes exclusively measuring data acquired while the radiation source irradiates the points within the examination zone from an angular range of exactly 180° as seen from the relevant point itself; the rays associated with the measuring data then pass exactly through the area between two adjacent turns of the helix. On the one hand this angular range suffices to enable exact reconstruction while on the other hand it avoids the use of redundant measuring data. The type of rebinning performed in relation to these measuring data is essential (rebinning is to be understood to mean the resorting of the measuring data from the sequence yielded by the acquisition as well as the re-interpolation of the measuring data on a different grid). Rebinning is performed with data having been acquired along rays which emanate from the same source point and form a fan beam extending in a plane parallel to the rotation axis. The subsequent processing steps, i.e. the preferably one-dimensional filtering and the reconstruction, are thus significantly facilitated.

In principle there are various possibilities for grouping the data emanating from the above-mentioned fan beams. For most of these groups, however, it will then be necessary to weight the measuring data with suitably chosen weighting factors (which may be dependent on the type of detector and on the type of rebinning). This necessity is eliminated, however, in the preferred version which is disclosed in claim 2 and in which each group contains only mutually parallel planes so that the further processing is significantly facilitated. Notably an outstanding image quality is thus obtained. In the further version according to claim 5, for each group the rebinning is performed on a virtual detector which extends perpendicularly to the planes associated with the relevant group and has a rectangular surface. The re-interpolation on an equidistant measuring point grid as required for the subsequent processing steps is thus significantly facilitated.

The absorption distribution could in principle be reconstructed from the filtered data of different groups by means of so-called generalized projections as described in the document published by Schaller et al. in SPIE, Vol. 3032, 32, pp. 213 to 224. A preferred type of reconstruction, however, is realized by back projection of the filtered data in conformity with claim 3.

The filtering operation could, also be performed, for example, by subjecting the data produced by the rebinning operation to a convolution with an appropriate filter kernel. The filtering operation defined in claim 4, however, requires less calculation time.

Claim 6 discloses a computer tomography apparatus for performing the method according to the invention and claim 7 defines an advantageous embodiment thereof. The shape of the collimator arrangement and/or the shape of the detector unit in this embodiment ensure that each point within the examination zone "sees" the radiation source, upon emerging from the radiation beam generated thereby, at an angle which has been shifted through exactly $180°(\Xi)$ with respect to the angle upon entering of the radiation beam. The advantage of this step resides in the fact that all measuring data required for an exact reconstruction is measured (and no other data). Thus, removal or co-weighting of redundant measuring data is not necessary.

BRIEF DESCRIPTION OF THE DRAWING

The invention will be described in detail hereinafter with reference to the drawings. Therein.

DETAILED DESCRIPTION OF THE PREFERRED EMBODIMENT

Figure 1:
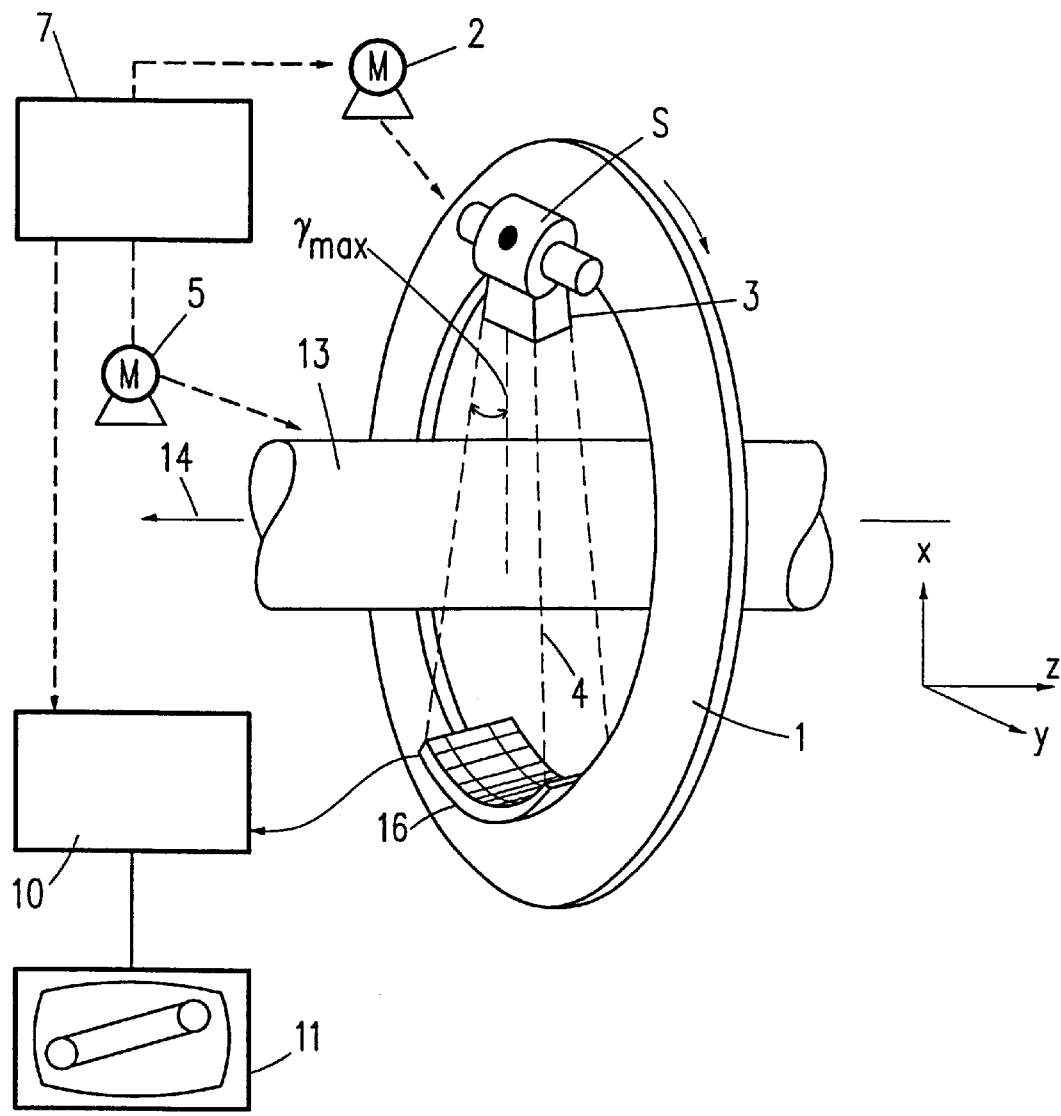
FIG. 1 is a diagrammatic representation of a computer tomography apparatus according to the invention.

The computer tomography apparatus shown in FIG. 1 includes a gantry 1 which is capable of rotation about an axis of rotation 14 which extends parallel to the z direction. To this end, the gantry is driven at a preferably constant angular speed by a motor 2. On the gantry there is mounted a radiation source S, for example an X-ray tube, which is provided with a collimator arrangement 3 which forms a conical radiation beam 4 from the radiation produced by the radiation source S, i.e. a radiation beam having a finite dimension in the direction of the z axis as well as in the direction perpendicular thereto (i.e. in the x-y plane of the Cartesian co-ordinate system shown in FIG. 1).

The radiation beam irradiates an examination zone 13 or (not shown) an object, for example a patient arranged on a patient table. After having traversed the examination zone 13, the X-ray beam 4 is incident on a two-dimensional detector unit 16 which is attached to the gantry 1 and comprises a plurality of detector rows, each of which comprises a plurality of detector elements. Each detector element detects a ray from the radiation beam 4 in each radiation source position. The detector unit 16 may be arranged on an arc of circle which coincides with the circular path of the radiation source S during the rotation.

The angle of aperture $K_{max}$ of the radiation beam 4 (the angle of aperture is to be understood to mean the angle enclosed by a ray of the beam 4 which is situated at the edge in the x-y plane relative to the ray which intersects the axis of rotation 14 at right angles) then determines the diameter of the examination zone 13 which is concentric with the axis of rotation 14 and in which the object to be examined must be present during the acquisition of the measuring values by means of the detector unit. The examination zone 13, or a patient who is arranged, for example on a patient table present therein, can be shifted parallel to the direction of the axis of rotation 14 or the z axis by means of a motor 5. The measuring data then acquired by the detector unit 16 is applied to an image processing computer 10 which derives therefrom the distribution of the absorption of the emitted radiation in the part of the examination zone 13 covered by the cone beam 4 and reproduces it, for example on a monitor 11. The two motors 2 and 5, the image processing computer 10, the radiation source S and the transfer of the measuring data from the detector unit 16 to the image processing computer 10 are controlled by means of an appropriate control unit 7.

The control unit 7 controls the motors 2 and 5 in such a manner that the ratio of the speed v of the examination zone 13 to the angular speed of the gantry 1 is constant. The radiation source S and the examination zone then move along a helical path relative to one another. It is then irrelevant in principle whether the scanning unit or the examination zone performs the rotation or translation; only the relative motion is of importance.

Figure 2:
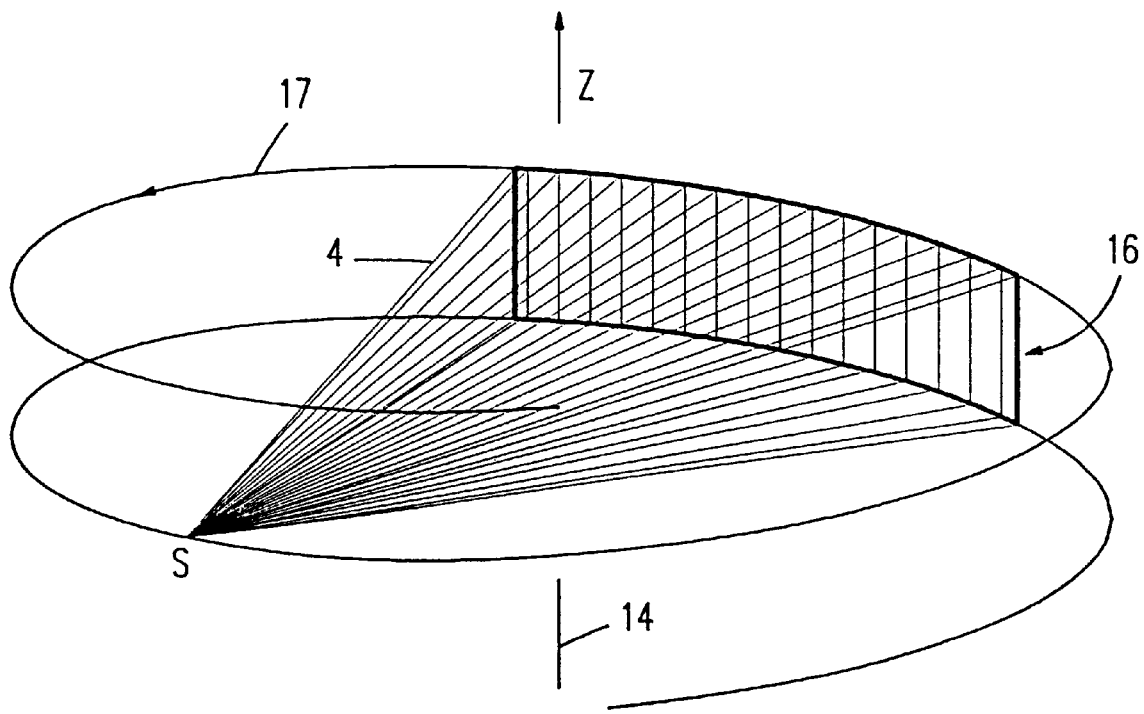
FIG. 2 shows the helical scanning path described relative to one another by the scanning unit and an object present in the examination zone.

Therefore, it has been assumed in FIG. 2 that the radiation source S (and the detector unit 16 connected thereto via the gantry) move along the helical path 17 in FIG. 2, whereas the examination zone 13 (or the object present therein) which is not shown in FIG. 2 is stationary. The conical radiation beam 4 emitted by the source S is incident on the detector unit 16 arranged to the other side of the examination zone. The conical beam 4 is depicted as if it contained a respective fan beam in a plurality of planes parallel to the axis of rotation 14 (or to the z direction). All of said flat fan beams emanate from the relevant position of the radiation source S or intersect one another in this position.

Figure 3:
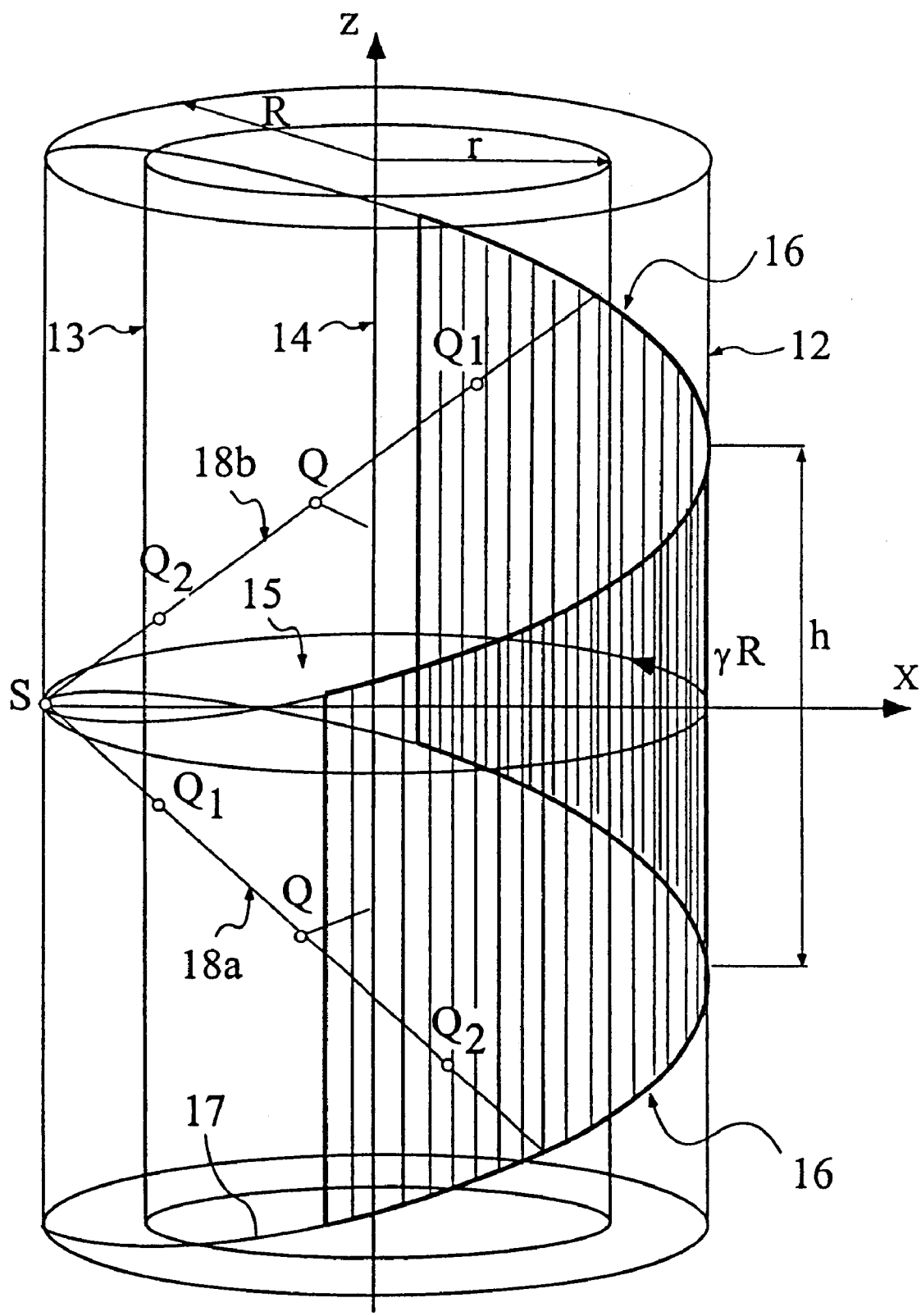
FIG. 3 is a perspective view of the scanning unit and the examination zone.

FIG. 3 is a perspective view of the radiation source S, symbolized by the point wherefrom the radiation emanates, the detector unit 16 and the cylindrical examination zone 13 having the radius r. Also shown is a cylinder 12 which concentrically encloses the examination zone 13 and has a radius R; the helical scanning path (17 in FIG. 2) is situated on this cylinder which, therefore, will also be referred to as the helix cylinder hereinafter. The detector unit 16, consisting of a mosaic of detector elements as indicated in FIG. 1 which may be arranged in columns (parallel to the axis of rotation 14) and rows, is situated on the circumference of the helix cylinder 12 between two successive turns of the helix 12; its dimensions in the z direction thus correspond to the pitch h of the turns of the helix. In this case it is assumed that the radiation source S and the detector unit 16 are stationary whereas the examination zone 13 with the object present therein is shifted in the direction of the axis of rotation 14 and at the same time rotates counterclockwise about this axis of rotation 14; the cylinder 13, therefore, would be shifted out of the helix cylinder 12 in the upwards direction.

FIG. 3 also shows two rays 18a and 18b which are incident on the lower edge and the upper edge, respectively, of the detector unit and pass through the boundary of the examination zone 13 at the points $Q_1$ and $Q_2$. The point Q on the ray between these points is the point on the ray which is situated at the shortest distance from the axis of rotation 14. The rays 18a and 18b strike the points $Q_1$-Q-$Q_2$ upon entering the radiation beam and upon leaving the radiation beam. Thus, they are detected by the detector unit at different instants.

Figure 4:
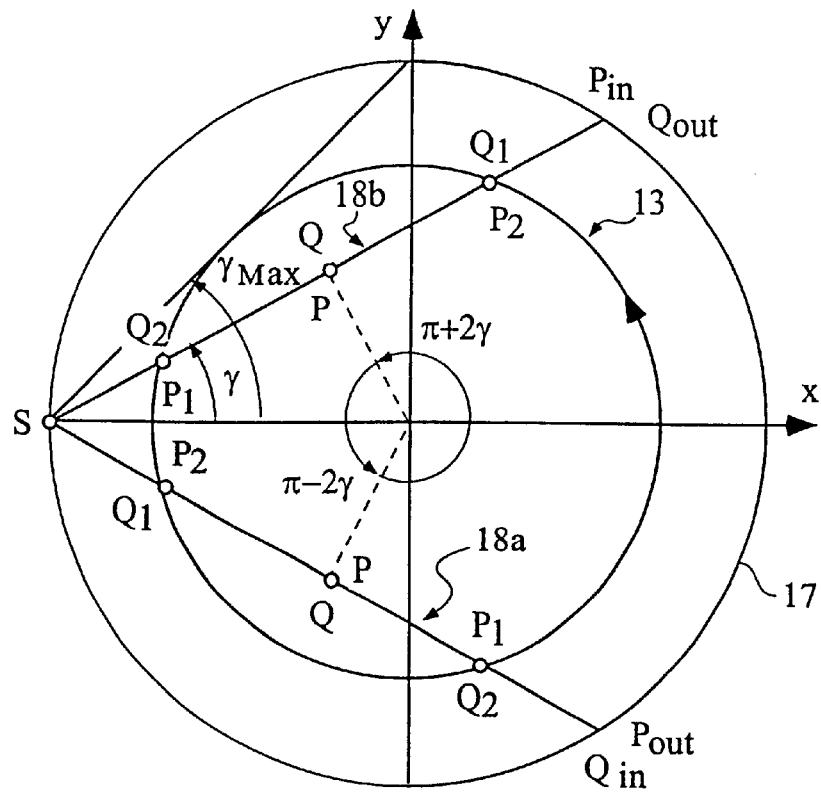
FIG. 4 is a plan view of FIG. 3.

FIG. 4 is a plan view of the arrangement of FIG. 3, i.e. a view taken parallel to the z axis or the axis of rotation 14. The angle of aperture $K_{max}$ of the cone beam in the direction of the x-y plane then amounts to 45°, meaning that the radius r=R/√2. However, the radius r may also be larger than R/√2 (but always smaller than R) or smaller as is shown in FIG. 1.

The projection of the two rays 18a and 18b on the x-y plane encloses an angle K with respect to the x axis, i.e. a ray emanating from S and passing through the axis of rotation 14. The lower ray 18a becomes the upper ray 18b after the examination zone 13 has been rotated through the angle $\Xi+2K$ and shifted proportionally in the z direction. However, whereas the point $Q_1$ is situated between the radiation source S and $Q_2$ upon entering of the radiation cone, exactly the reverse situation occurs upon leaving.

This means that the points $Q_1$ and $Q_2$, and all other points on the line through $Q_1$ and $Q_2$, have been irradiated or projected onto the detector unit 16 in an angular range of exactly 180°, viewed from the relevant point. A line with points simultaneously entering and simultaneously leaving the examination zone 13 in this manner is called a II-line. The line 18 in FIG. 3 and FIG. 4 is such a II-line and it will be evident that a II-line is any line intercounting two points on the same turn of the helical scanning path 17. It can be demonstrated that each point in the examination zone belongs to one II-line and one II-line only. Therefore, each point is irradiated from an angular range 180° viewed from this-point itself. This suffices (and is necessary) to enable reconstruction of each point within the examination zone 13 which has entered and emerged from the cone beam. The detector unit 16 thus delivers the measuring values required for exact reconstruction, but no redundant measuring values so that the reconstruction is considerably simplified.

Figure 5:
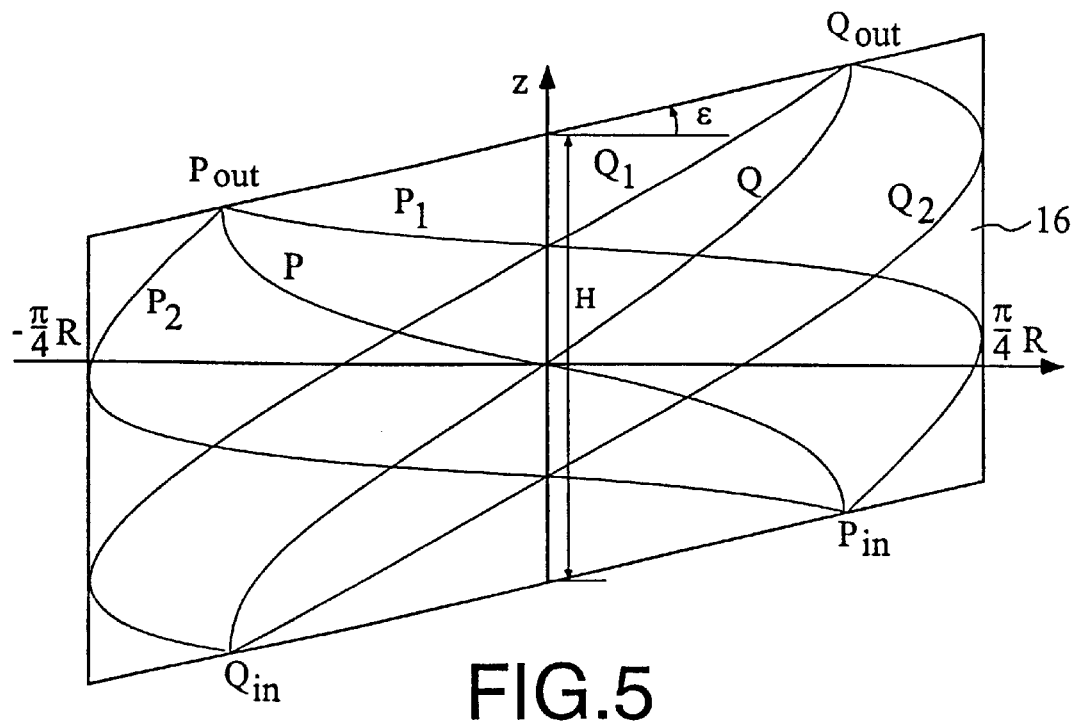
FIG. 5 is a developed view of the detector unit.

FIG. 5 is a developed view of a detector unit 16 from the helix cylinder 12 in the plane of drawing. The development is formed as a parallelogram having sides extending parallel to the z direction; the upper and the lower side enclose an angle M relative to the axis of rotation in conformity with the slope of the helix, which angle M can be calculated from the relation $\tan M = h/2\Xi R$. In this respect it is assumed that the speeds of translation and rotation (or the angular speed) are constant and that a complete rotation about the axis of rotation 14 takes place in the same period of time in which a displacement over the distance h takes place in the z direction.

During the passage of the cone beam by a point, its projection on the detector unit 16 continuously changes position. Starting at the lower edge (or at the lower detector row) of the detector unit, it describes a curve on the detector unit which terminates at the upper edge. FIG. 5 shows the curves for the points $Q_1$, Q and $Q_2$. FIG. 5 also shows the curves for the points on another II-line with the points $P_1$, P, $P_2$ whose projection in the z direction coincides with the upper ray 18b in FIG. 4 upon entering the radiation beam (i.e. when their connecting line to the radiation source intersects the lower edge of the detector unit, see FIG. 3). These points are situated nearer to the radiation source S than the points $Q_1$-Q-$Q_2$ during their passage through the cone beam, and they pass the cone beam during a rotation through the angle $\Xi-2K$ about the axis of rotation 14. During their passage through the cone beam 4 these points nevertheless also "see" the radiation source S from an angle of exactly 180°. The greater the distance between two points on the same II-line, the greater the difference will be between the two curves described by these two points on the detector.

The development of the detector unit need not necessarily have the shape of a parallelogram as shown in FIG. 5. Use could also be made of a larger, for example rectangular detector if the collimator 3 (FIG. 1) limits the conical radiation beam of the radiation source S in such a manner that the development of the area of the detector unit struck by the radiation beam has exactly the shape shown in FIG. 5. Instead of this step, or in combination therewith, the measuring data from the detector elements which are situated outside the parallelogram on the detector of FIG. 5 can be ignored.

Figure 6:
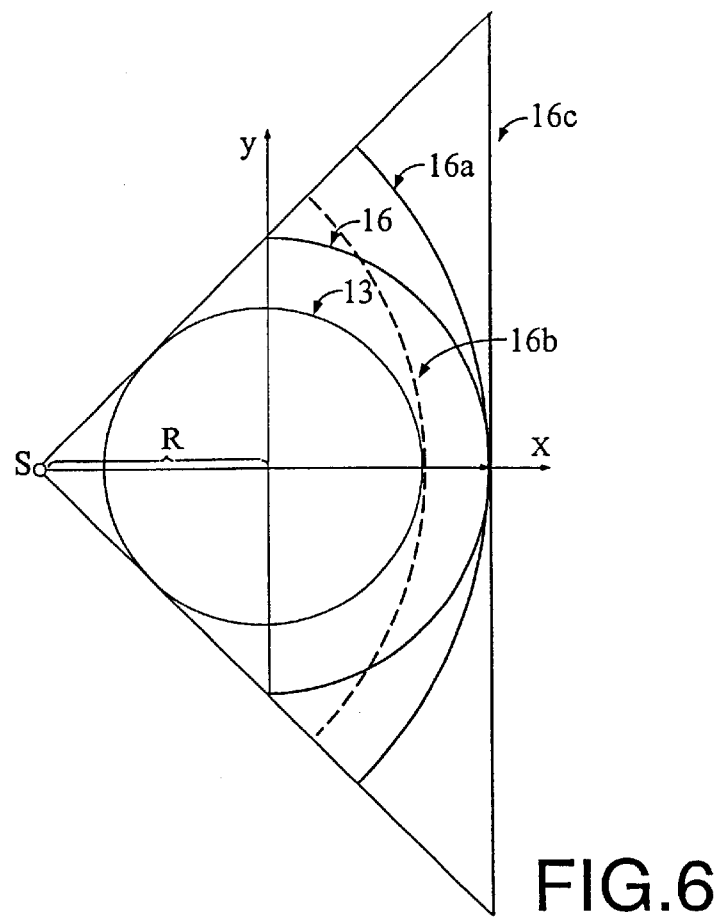
FIG. 6 illustrates various possibilities for the arrangement of the detector unit.

It is not necessary either for the detector elements to be situated on the circumference of the helix cylinder 12 (FIG. 3). As is indicated in FIG. 6, diagrammatically representing a parallel projection of the arrangement of FIG. 3 in the direction of the z axis, the detector unit can also describe a helical arc of circle 16b or 16a about the radiation source S which is tangent to the examination zone 13 or the helix cylinder. The detector unit may also have a flat surface 16c or be shaped arbitrarily. For all these versions it is essential only that the edges of the detector unit (or the respective area of the detector unit on which the radiation beam 4 is incident) coincide with the central projection of two segments of a turn of the helical scanning path 17, or that each point "sees" the radiation source in an angular range of exactly 180° during its passage.

Figure 7:
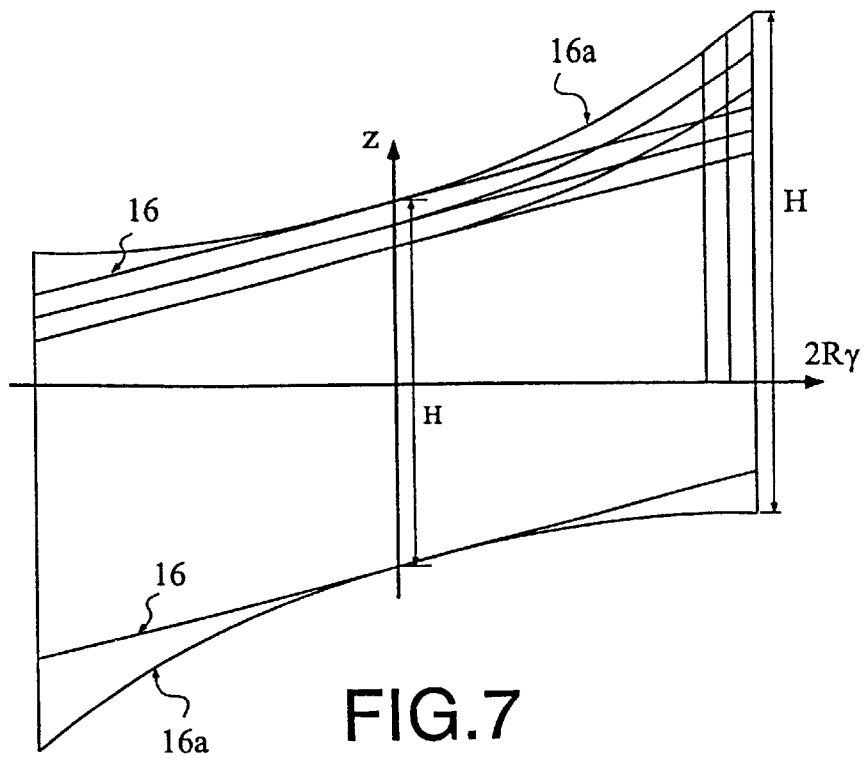
FIG. 7 is a developed view of a detector unit situated on a cylinder around the radiation source.

FIG. 7 shows the developed views of the detector units 16 and 16a in the plane of drawing which are tangent to the helix cylinder 12 on an arc of circle around the radiation source. It appears that the height of this development, i.e. the dimension in the direction of the z axis, varies and analogously do the dimensions of the detector rows, i.e. in conformity with the function h/cosK, where K is the angle enclosed by the projection of a ray in the x-y plane relative to the z axis (for example, see FIG. 4).

Figure 9:
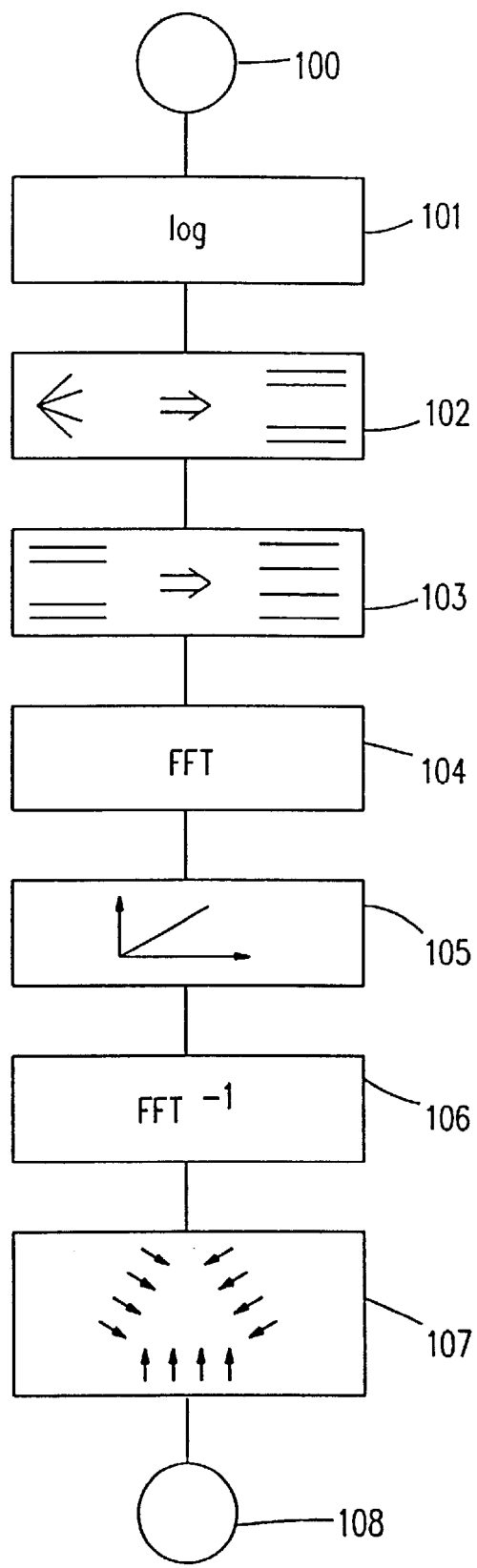
FIG. 9 shows a flow chart illustrating the processing of the measuring data.

The further processing by the image processing computer 10 of the data acquired by the multi-row detector unit 16 will be described in detail hereinafter with reference to the flow chart shown in FIG. 9. After the initialization (block 100), each measuring value from each detector element is first divided by a reference value and the resultant quotient is logarithmized. The measuring data thus formed represents the line integral of the absorption of the radiation along a ray connecting the radiation source to the relevant detector element. The subsequent processing steps serve to determine the spatial distribution of the absorption from these line integrals of the absorption.

To this end, first a rebinning operation is performed. After the rebinning, or before that, the measuring data is weighted in that this data is mutliplied by a factor which corresponds to the cosine of the angle enclosed by the ray (for example, 18) associated with the measuring data relative to a plane intersecting the axis of rotation at right angles. This weighting step, however, can be omitted in those cases where the distance between two turns of the helix is small in comparison with their radius. Therefore, this step is not shown separately in FIG. 9.

Figure 10:
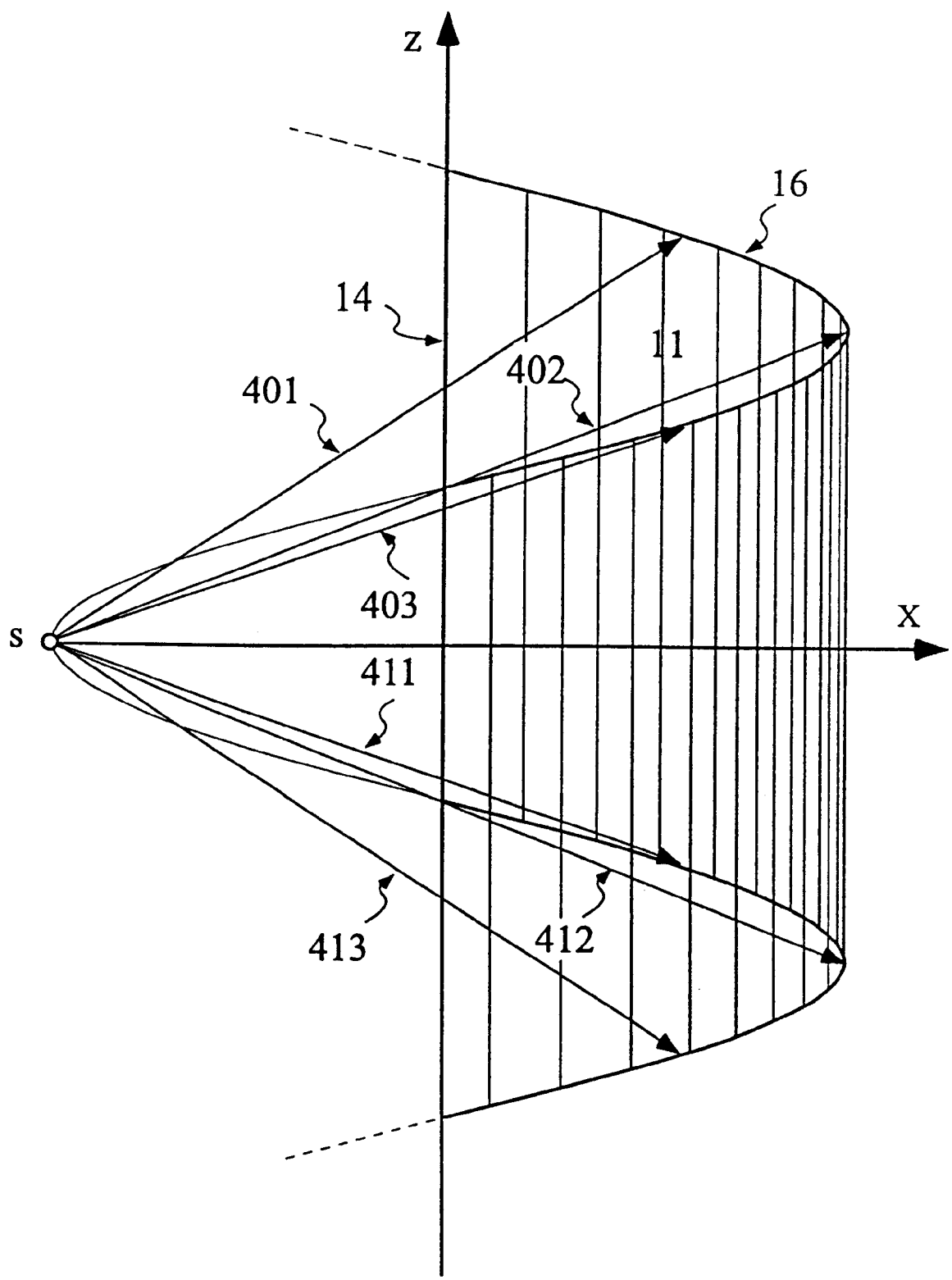
FIG. 10 is a side elevation of the detector units with some rays.

During the rebinning operation, in a first step 102, there are formed groups of fan beams which are situated in planes parallel to one another and parallel to the axis of rotation 14, or groups of measuring data associated with the rays constituting these fan beams. This will first be described with reference to FIG. 10 which is a side elevation of the arrangement shown in FIG. 3. FIG. 10 shows six rays of the conical beam 4; three rays 401 . . . 403 thereof strike the upper edge while three rays 411 . . . 413 strike the lower edge of the detector unit. The rays 402 and 412 pass through the axis of rotation 14 whereas the rays 401, 403, and 411, 413 pass the axis of rotation to the left and to the right, respectively. Each time two of these rays constitute the edge rays of a fan beam whose rays are situated in a plane parallel to the z axis or axis of rotation 14, for example the rays 401 and 411, the rays 402 and 412 and the rays 403 and 413.

Figure 11:
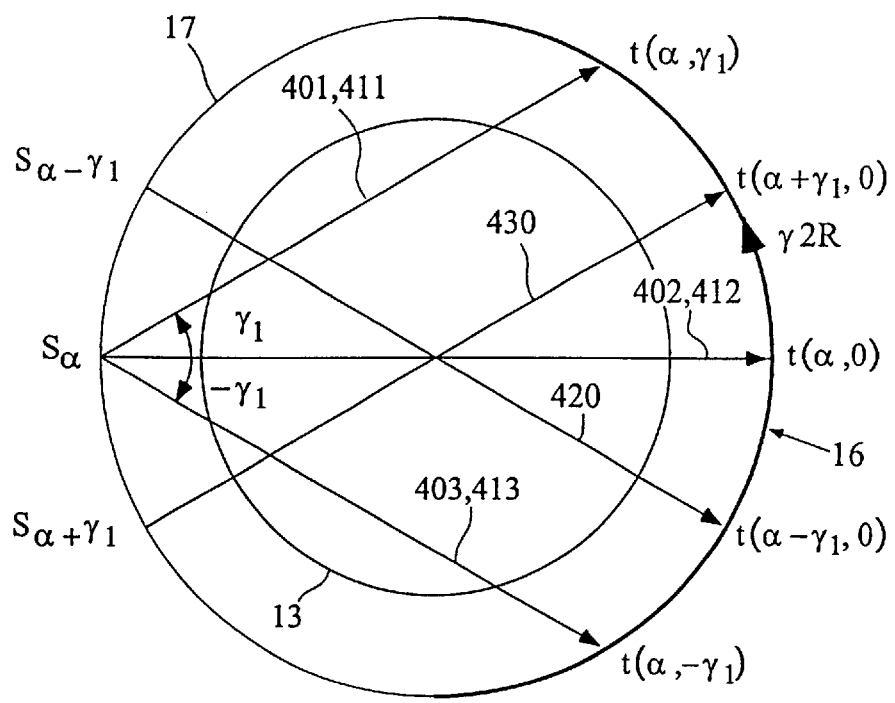
FIG. 11 is a plan view of the arrangement shown in FIG. 10.

FIG. 11 is a plan view of the arrangement shown in FIG. 10. Because the rays 401 . . . 403 and 411 . . . 413 are situated in the same plane, extending perpendicularly to the plane of drawing of FIG. 11, they appear as a single ray in FIG. 11.

The planes defined by these fan beams intersect one another in the radiation source position $S_I$. The plane containing the fan beams 401, 411 encloses an angle $+K_1$ relative to the central plane containing the axis of rotation, whereas an angle $-K_1$ exists between the central plane and the planes of the fan beam 403, 413. The fan beam 402, 412 is identical to the central plane (being the x-z plane in FIG. 11).

FIG. 11 shows two further radiation source positions $S_{I-K_1}$ and $S_{I+K_1}$ to both sides of the central radiation source position $S_I$, and a respective fan beam which emanates from this source position and passes through the axis of rotation 14 by way of the fan beams 420 and 430, respectively. It appears that the fan beams 420 and 403, 413 extend parallel to one another, like the fan beams 401, 411 and 430. According to the invention in the step 102 the fan beams from different radiation source positions being situated in planes parallel to one another (and to the axis of rotation 14), or the measuring data associated with the rays constituting these fan beams, are combined so as to form a respective group. Thus, combined in one group are those fan beams (and associated measuring values) for which the sum of the angle characterizing the radiation source position (I or I-$K_1$ or I+$K_1$) and the fan angle K (being the angle enclosed by the plane of the fan beam relative to a plane containing the axis of rotation 14; these are, for example the angles $-K_1$ and $+K_1$, respectively, in FIG. 11) is constant.

In practice only discrete values occur for the angle I of the radiation source positions or, due to the finite dimensions of the detector elements, of the fan angle K. These discrete values deviate from one another by increments dI and dK; it may be that dI≠dK. Because of this inequality, the sum of these two angles cannot always have exactly the same value for different radiation source positions; fan beams may occur for which the sum is slightly larger or slightly smaller than the angle I associated with the central radiation source position $S_I$, i.e. the associated fan beams are not situated in parallel planes. In that case interpolation can be applied so as to derive measuring data corresponding to a fan beam which is situated in an exactly parallel plane or for which the sum is exactly α, using measuring data corresponding to these original fan beams which deviate slightly from the angle α.

Figure 12:
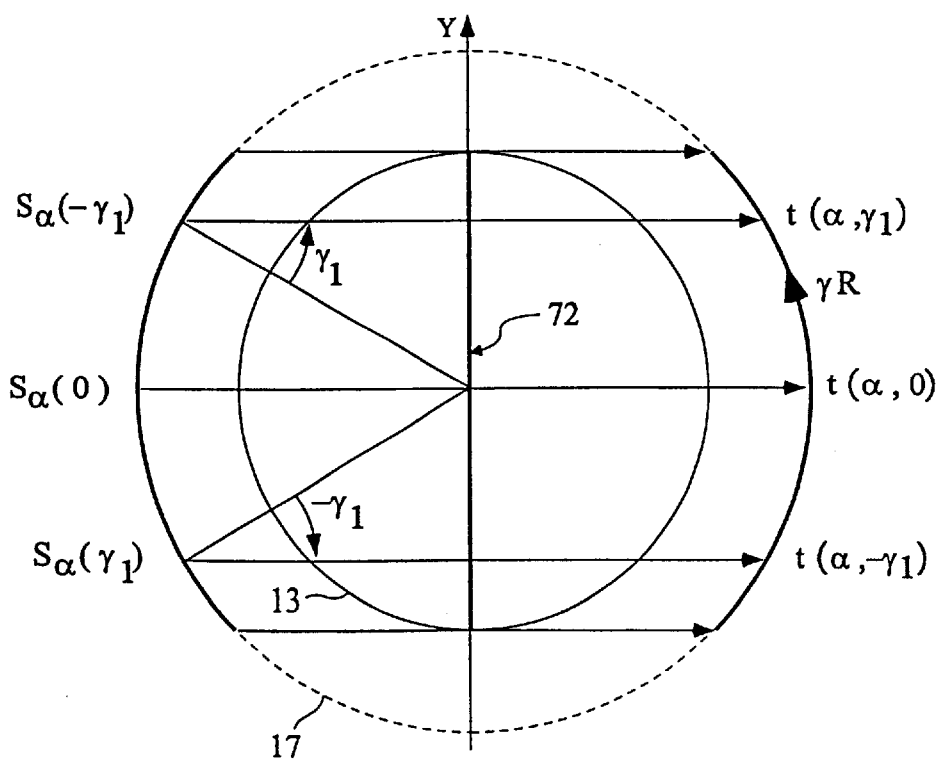
FIG. 12 shows the same plan view as FIG. 11, be it after partial rebinning of measuring data.

FIG. 12 shows such a set of fan beams, generated in different radiation source positions and situated in parallel planes extending through the examination zone 13. A virtual detector 72 is arranged perpendicularly to the planes in which said fan beams are situated and in the axis of rotation. The dimensions of this virtual detector in the x-y plane correspond to the diameter of the examination zone 13 (2r). The dimensions of the virtual detector in the z direction amount to h/2. This is because it can be demonstrated that the upper and lower edge rays of all fan beams coincide exactly with the upper edge and the lower edge (in the z direction) of this flat, virtual and exactly rectangular detector.

Figure 8:
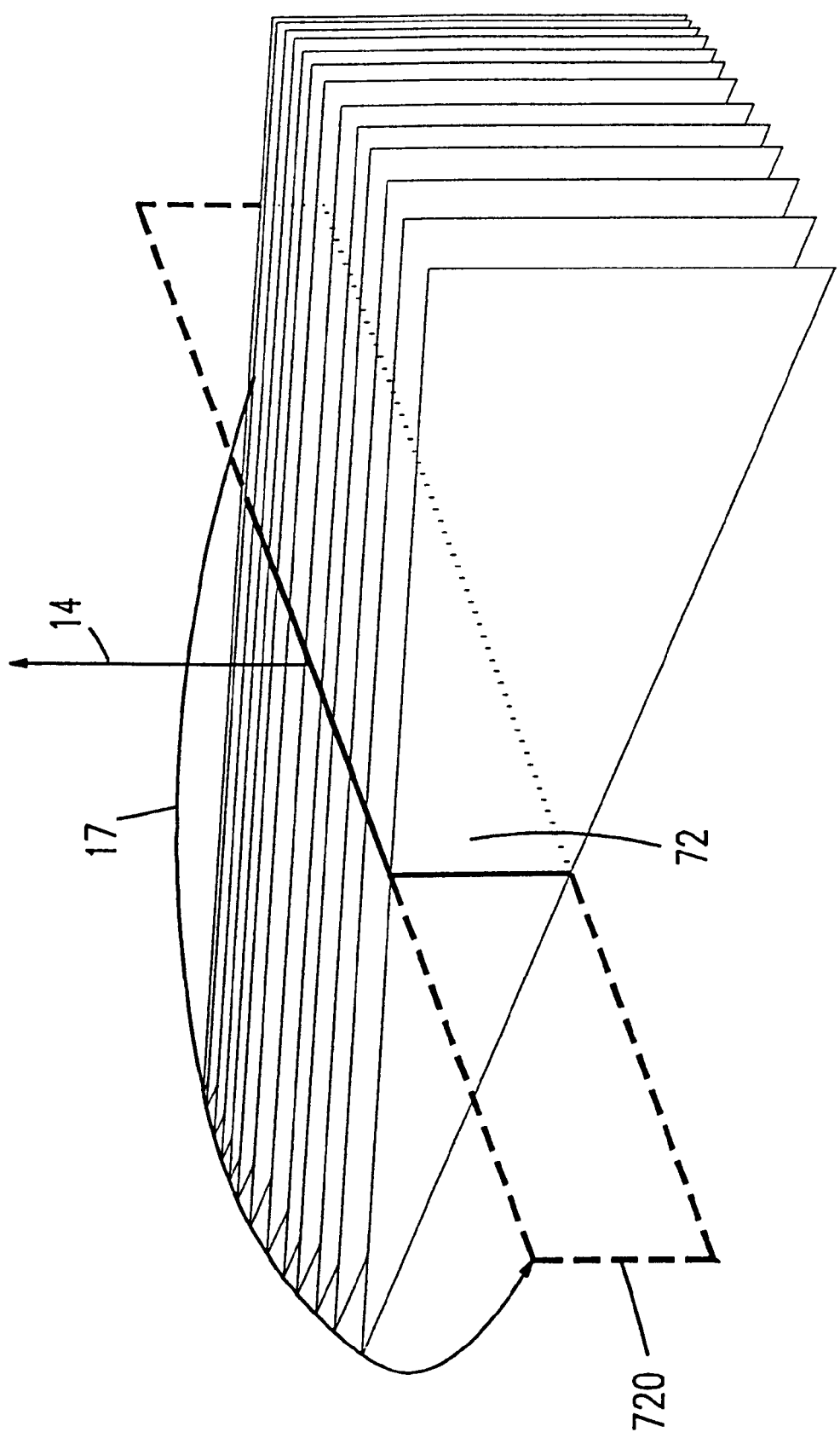
FIG. 8 is a perspective view of fans associated with a group of rebinned data.

FIG. 8 is a perspective representation of the configuration, it being assumed that the radiation source moves along the helical path 17. The upper and the left-hand side of the virtual detector 72 are denoted by solid lines, whereas the lower side is represented by a dotted line. The upper edge and the lower edge of the virtual detector 72 are extended by way of dashed lines 72 so as to form a rectangle 720; the helical path 17 extends from the lower right-hand corner point to the upper corner point thereof. The fan beams, emanating from different radiation source positions on the helical path and extending in mutually parallel planes, are represented as triangles whose upper and lower sides denote the upper and the lower edge ray of the fan beam and whose vertical side is intended to denote the position of the column of the detector unit which is struck by the relevant fan beam.

Even though the radiation source positions to the left and to the right of the center are situated higher and lower (measured in the direction of the axis of rotation), respectively, than the central radiation source position, the upper and the lower edge rays enter the upper and the lower edge of the plane virtual detector 72. This is due to the fact that the fan beams situated to the right and to the left of the center are intercepted by detector columns which are situated higher and lower, respectively, in the z direction than the column which detects the fan beam which emanates from the central radiation source position and passes through the axis of rotation 14.

It will be evident from the foregoing that each fan beam covers a column of the virtual detector. During the step 102 all fan beams (situated in planes parallel to the axis of rotation) are assigned to a respective one of the groups so that, possibly after interpolation, each group contains fan beams situated in parallel planes which perpendicularly intersect the virtual detector 72 associated with the relevant group.

After all measuring data and the associated fan beams have thus been detected for at least one group, in the step 103 the second part of the rebinning operation is performed. This is a further interpolation operation which is required because of the following. The fan beams cover a vertical strip or a column in the virtual detector and the rays associated with a fan beam can be incident on the virtual detector at equidistant points, but the columns or vertical strips are situated at different distances from one another (for reasons of geometry they are situated nearer to one another at the outer side than at the inner side). Therefore, in the step 103 the data produced by the step 102 is interpolated in such a manner that the associated rays and the associated line integrals of the absorption are obtained for a regular Cartesian grid on the virtual detector. This completes rebinning with a parallel beam geometry on a rectangular detector surface with regularly distributed grid points, so that the subsequent processing is significantly facilitated.

The rebinning operation carried out in the steps 102 and 103 thus produces groups of measuring data and the associated rays, which would occur if a flat, rectangular detector in a plane containing the axis of rotation 14 (i.e. the virtual detector) were to acquire the measuring data of a radiation source extending along a segment of the line 17 and emitting fan beams extending perpendicularly to the detector plane and parallel to the axis of rotation 14.

Subsequently, a one-dimensional filtering operation is performed in the step 104. For the given rebinning operation, merely a simple, one-dimensional, location-independent, preferably ramp-like filter is required in the line direction (the line direction extends vertically in the representation of FIG. 12, or in the longitudinal direction of the rectangle 720, 72 in the perspective view of FIG. 8, and hence perpendicularly to the axis of ration 14). The filtering operation can in principle be carried out by subjecting the data resulting from the rebinning operation to a convolution with a suitable one-dimensional filter kernel.

A simpler possibility, however, consists in subjecting the data produced by the rebinning operation to a Fourier transformation first in the step 104. In the step 105 the data thus transformed in the spatial frequency domain is subjected to a ramp-like filtering operation (in the line direction) during which the damping decreases linearly as the value of the frequency increases. In the step 106 the data thus filtered in the spatial frequency domain is subjected to an inverse Fourier transformation, yielding filtered projection data.

It is not essential that the virtual detector on which the rebinning is based is flat and contains the axis of rotation. The puncture points of the individual rays and the (virtual) detector then no longer describe lines perpendicular to the axis of rotation, but possibly curved lines. In that case it is necessary to use for the filtering operation the measuring data which is associated, within the fan beams associated with the same group, with the corresponding rays (for example, the each time upper rays, the upper rays but one the lower rays). During the next step 107 the filtered data of each group is backprojected into the spatial domain. The filtered data is thus assigned to the voxels in the examination zone (i.e. it is "spread" among these voxels) which were struck by the associated beam during the acquisition. Each voxel thus receives contributions from different groups of rays (or the associated data) which, in respect of this voxel, enclose an angle of 180° relative to one another.

This already yields a complete reconstruction of a part of the examination zone as soon as the measuring data produced by one pass of the scanning unit through an angle of $180°+2K_{max}$, relative to the examination zone, has been processed in conformity with the steps 101–107. The region thus reconstructed can be displayed on the monitor immediately thereafter; during this display measuring data can still be acquired and processed in conformity with the steps 101 to 107. The acquisition of the measuring data and the reconstruction of the absorption distribution in the examination zone can then be terminated at an arbitrary instant (block 108).

All references cited herein are incorporated herein by reference in their entirety and for all purposes to the same extent as if each individual publication or patent or patent application was specifically and individually indicated to be incorporated by reference in its entirety for all purposes.

What is claimed is:

1. A computer tomography method which involves helical scanning of an examination zone by means of a scanning unit which includes a radiation source (S) and a detector unit (16), an object present in the examination zone (13) and the scanning unit simultaneously rotating about an axis of rotation relative to one another and performing a motion parallel to the direction of the axis of rotation, resulting in a relative motion in the form of a helix (17), and also involves a reconstruction of the spatial distribution of the absorption within the examination zone from the measuring data acquired by the detector unit, characterized in that it includes the following steps
   a) using exclusively the measuring data for the reconstruction which are obtained from rays which pass exactly through the area between two adjacent turns of the helix, the points within the examination zone thereby being irradiated over an angular range of exactly 180 degrees—as seen from the point itself,
   b) rebinning the measuring data and the associated rays so as to form a number of groups, each group comprising a plurality of planes which extend parallel to the axis of rotation and each of which contains a respective fan beam,
   c) filtering the data of each group, formed by the rebinning,
   d) reconstructing the spatial distribution of the absorption from the filtered data of different groups.

2. A computer tomography method as claimed in claim 1, characterized in that the measuring data is rebinned in such a manner that the planes containing a respective fan beam in each group extend parallel to one another and to the axis of rotation.

3. A computer tomography method as claimed in claim 1, characterized in that the reconstruction step includes the backprojection of the filtered data of a plurality of groups.

4. A computer tomography method as claimed in claim 2, characterized in that the filtering operation includes the following steps:
   a) one-dimensional Fourier transformation of the data of each group in the direction perpendicular to the axis of rotation,
   b) application of a ramp filter to the values yielded by the Fourier transformation,
   c) inverse Fourier transformation of the filtered data.

5. A computer tomography method as claimed in claim 1, characterized in that the rebinning is performed on a respective flat virtual detector which extends perpendicularly to the planes of each group and contains the axis of rotation.

6. A computer tomography apparatus for carrying out the method claimed in claim 1, provided with a scanning unit which includes a radiation source and a detector unit connected thereto, a drive device for simultaneously rotating an object present in the examination zone and the scanning unit relative to one another about an axis of rotation and for causing them to perform a motion in the direction of the axis of rotation, and also with a reconstruction unit for reconstructing the spatial distribution of the absorption within the examination zone from the measuring data acquired by the detector unit, characterized in that it includes
   a) means for using exclusively measuring data for the reconstruction which has been acquired during irradiation of the points within the examination zone from an angular range of 180°, the radiation source,
   b) means for rebinning the measuring data so as to form a plurality of groups, each group containing a plurality of planes which extend parallel to the axis of rotation and in which a respective fan beam is situated,
   c) means for the one-dimensional filtering of the data produced by the rebinning operation of each group in the direction perpendicular to the axis of rotation,
   d) means for the reconstruction of the spatial distribution of the absorption from the filtered data of different groups.

7. A computer tomography apparatus as claimed in claim 6, characterized in that a collimator arrangement and/or detector unit is constructed in such a manner that all connecting lines between the radiation source and the angula range, mutually offset in the direction of rotation, of the area of the detector unit struck by the radiation beam, or the detector unit, intersect two segments of a turn of the helix which neighbor one another in the direction of rotation and along which the radiation source and the object are movable relative to one another.

* * * * *